US011786656B2

(12) United States Patent
Yu et al.

(10) Patent No.: US 11,786,656 B2
(45) Date of Patent: Oct. 17, 2023

(54) CLOUD BIG DATA-BASED SYSTEM AND METHOD FOR INSULIN PUMP INDIVIDUALIZED CONFIGURATION OPTIMIZATION

(71) Applicant: MICROTECH MEDICAL (HANGZHOU) CO., LTD., Hangzhou (CN)

(72) Inventors: Fei Yu, Hangzhou (CN); Zhiyan Chen, Hangzhou (CN); Jianfeng Lv, Hangzhou (CN)

(73) Assignee: MICROTECH MEDICAL (HANGZHOU) CO., LTD., Hangzhou (CN)

( * ) Notice: Subject to any disclaimer, the term of this patent is extended or adjusted under 35 U.S.C. 154(b) by 723 days.

(21) Appl. No.: 16/967,647

(22) PCT Filed: Oct. 8, 2018

(86) PCT No.: PCT/CN2018/109282
§ 371 (c)(1),
(2) Date: Aug. 5, 2020

(87) PCT Pub. No.: WO2019/072141
PCT Pub. Date: Apr. 18, 2019

(65) Prior Publication Data
US 2021/0187195 A1    Jun. 24, 2021

(30) Foreign Application Priority Data
Oct. 12, 2017   (CN) .................. 201710947229.X

(51) Int. Cl.
*A61M 5/172*   (2006.01)
*G16H 20/17*   (2018.01)
(Continued)

(52) U.S. Cl.
CPC ...... *A61M 5/1723* (2013.01); *A61M 5/14276* (2013.01); *A61M 5/16877* (2013.01);
(Continued)

(58) Field of Classification Search
CPC ............ A61M 5/1723; A61M 5/14276; A61M 5/16877; A61M 2005/14252;
(Continued)

(56) References Cited

U.S. PATENT DOCUMENTS

2006/0031094 A1* 2/2006 Cohen .................... G16H 20/30
705/2
2012/0232520 A1* 9/2012 Sloan ............... G01N 33/48792
604/504

(Continued)

FOREIGN PATENT DOCUMENTS

CN   101254322 A   9/2008
CN   102016855 A   4/2011
(Continued)

*Primary Examiner* — Kenneth Bartley
(74) *Attorney, Agent, or Firm* — Bayramoglu Law Offices LLC

(57) ABSTRACT

A cloud big data-based system and method for insulin pump individualized configuration optimization are provided. The system includes an insulin pump, a real-time continuous glucose monitoring system, a smart phone, a glucose monitoring application software installed in the smart phone and a cloud big data server. By means of personal blood glucose measurement historical data of users stored in the cloud, the insulin pump individualized configuration optimization system provides effective calculation of an individualized optimal insulin injection volume and injection rate for each user, thus aiding physicians and patients to formulate diabetes treatment plans with increased effectiveness.

6 Claims, 2 Drawing Sheets

(51) Int. Cl.
  *A61M 5/142* (2006.01)
  *A61M 5/168* (2006.01)
  *G16H 20/10* (2018.01)
  *G16H 40/60* (2018.01)

(52) U.S. Cl.
  CPC ............. *G16H 20/10* (2018.01); *G16H 20/17* (2018.01); *G16H 40/60* (2018.01); *A61M 2005/14252* (2013.01); *A61M 2005/14284* (2013.01); *A61M 2205/3553* (2013.01); *A61M 2205/3561* (2013.01); *A61M 2205/52* (2013.01); *A61M 2230/201* (2013.01)

(58) Field of Classification Search
  CPC ........... A61M 2005/14284; A61M 2205/3553; A61M 2205/3561; A61M 2205/52; A61M 2230/201; A61M 5/142; A61M 5/168; G16H 20/17; G16H 20/10; G16H 40/60; G16Y 10/60; G06N 7/01; G06N 33/66; G01N 2800/042
  See application file for complete search history.

(56) References Cited

U.S. PATENT DOCUMENTS

| | | | |
|---|---|---|---|
| 2013/0179186 A1* | 7/2013 | Birtwhistle | G16H 10/60 705/3 |
| 2014/0180238 A1 | 6/2014 | Imhof et al. | |
| 2016/0073952 A1 | 3/2016 | Bashan et al. | |
| 2017/0189614 A1 | 7/2017 | Mazlish et al. | |
| 2017/0203037 A1 | 7/2017 | Desborough et al. | |
| 2019/0252079 A1* | 8/2019 | Constantin | A61B 5/0024 |
| 2020/0027544 A1* | 1/2020 | Booth | G16H 20/17 |
| 2020/0402636 A1* | 12/2020 | Booth | G16Z 99/00 |

FOREIGN PATENT DOCUMENTS

| | | | | |
|---|---|---|---|---|
| CN | 102500013 | A | | 6/2012 |
| CN | 103154849 | A * | 6/2013 | ......... A61B 5/14532 |
| CN | 103238154 | A * | 8/2013 | ........... G06F 19/323 |
| CN | 104010565 | A * | 8/2014 | ........... A61B 5/0002 |
| CN | 103418053 | B | | 3/2015 |
| CN | 104520862 | A * | 4/2015 | ......... A61B 5/14532 |
| CN | 103533889 | B * | 11/2016 | ......... A61B 5/14532 |
| CN | 106730153 | A | | 5/2017 |
| CN | 107073207 | A * | 8/2017 | ......... A61B 5/14532 |
| CN | 107073207 | A | | 8/2017 |
| CN | 107135644 | A | | 9/2017 |
| CN | 107715230 | A * | 2/2018 | ............ A61M 5/142 |
| CN | 108292525 | A * | 7/2018 | ........... A61B 5/0022 |
| CN | 108601890 | A * | 9/2018 | ......... A61B 5/14532 |
| CN | 110402156 | A * | 11/2019 | ........... A61B 5/0004 |
| EP | 3567594 | A1 * | 11/2019 | ....... A61M 5/14244 |
| ES | 2741173 | T3 * | 2/2020 | .......... A61M 5/1723 |
| KR | 20130042001 | A * | 4/2013 | |
| KR | 20130042596 | A * | 4/2013 | |
| WO | WO-2016008997 | A1 * | 1/2016 | ......... A61B 5/14532 |
| WO | WO-2017184988 | A1 * | 10/2017 | ............... A61B 5/00 |

\* cited by examiner

CLOUD BIG DATA-BASED SYSTEM AND METHOD FOR INSULIN PUMP INDIVIDUALIZED CONFIGURATION OPTIMIZATION

CROSS REFERENCE TO THE RELATED APPLICATIONS

This application is the national phase entry of International Application No. PCT/CN2018/109282, filed on Oct. 8, 2018, which is based upon and claims priority to Chinese Patent Application No. 201710947229. X, filed on Oct. 12, 2017, the entire contents of which are incorporated herein by reference.

TECHNICAL FIELD

The present invention relates to the technical field of intelligent medical devices, and in particular, to a cloud big data-based system and method for insulin pump individualized configuration optimization.

BACKGROUND

Diabetes can cause numerous health issues. It is a disease with the characteristic of excessively high glucose content in the blood caused by insulin deficiency (type 1 diabetes) or insulin resistance or decreased insulin secretion rate (type 2 diabetes). All patients with type 1 diabetes and most patients with advanced type 2 diabetes require in vitro insulin injections to control blood glucose. Continuous subcutaneous insulin infusion (CSII), also known as insulin pump therapy, is designed to mimic physiological insulin secretion by continuous insulin infusion using an artificial intelligence-controlled insulin infusion device so as to control hyperglycemia. Insulin secretion can be divided into two parts according to its relationship with eating: (i) a continuous micro secretion having no connection with meals, that is, the basal insulin secretion; and (ii) the large amount of insulin secretion caused by the increased blood glucose after meals.

In order to mimic physiological insulin secretion, the insulin pump is controlled by artificial intelligence to perform the basic rate insulin injection via the adjustable pulse subcutaneous infusion mode. At the same time, the patients set the pre-meal large dose insulin and infusion mode according to the type and total amount of food to control the postprandial blood glucose. Clinical studies have confirmed that compared with multiple insulin injections, insulin pump can control the level of glycosylated hemoglobin more effectively and improve the quality of life of patients.

Insulin pump has the following characteristics:

(1) It is more conducive to accurate and stable control of blood glucose, and reduces the fluctuation of blood glucose, which significantly reduces the risk of hypoglycemia and decreases the variation of insulin absorption.

(2) It improves the quality of life of patients. The use of insulin pump can improve the compliance of patients with treatment, reduce the pain and inconvenience caused by multiple injections of insulin, increase variations in one's diet and exercise, improve one's ability to self-manage their blood glucose levels as well as relieve the psychological burden of being a diabetic.

In contrast to injecting long-acting insulin and quick-acting insulin multiple times, the dosage and infusion rate of CSII insulin injection pump can be adjusted by patients at any time. Blood glucose and insulin levels in the human body are in a constant process of dynamic balance and are affected by many factors. How to determine the dose of insulin injection pump has been one of the research focuses of diabetes treatment. The infusion regimen recommended by the insulin pump therapy guidelines for China (2009) can be summarized as follows. First, the initial dose should be determined according to the type of diabetes, blood glucose level and body weight, and then be allocated to the basic infusion volume and pre-meal large dose. Then, the large dose should be supplemented and corrected according to the actual situation of the patient to comprehensively control the blood glucose.

When beginning an insulin injection pump regimen, the basic infusion volume, pre-meal large dose, supplementary large dose, correction large dose, and the time period of basic infusion rate are typically set according to specification or experience. Among these, the basic infusion volume refers to the amount of insulin needed to maintain the body's basal glucose metabolism, which can be adjusted by adjusting the basic infusion rate and corresponding time period. Basic infusion rate refers to the rate at which the insulin pump provides basal insulin, which is generally expressed in units of insulin dosage (U)/h. There are many setting modes, which can be set to one or more time periods according to the needs of blood glucose control. Most clinical trials are divided into 3-6 time periods. Compared with type 2 diabetes mellitus (T2DM) patients, type 1 diabetes mellitus (T1DM) patients generally need more time periods. Among the T2DM patients, the time periods divided for the so-called fragile DM patients with large blood glucose fluctuations are often different from those for ordinary patients. The infusion volumes including the pre-meal large dose, supplementary large dose and correction large dose are set by the patients themselves according to the current carbohydrate intake and their own physiological parameters, such as insulin-carbohydrate metabolism ratio, insulin sensitivity and other factors.

It is clinically difficult to determine and timely adjust the optimal insulin infusion volume for patients due to the huge individual differences between patients and the constantly varying physiological parameters of patients with the onset and development of the disease. As a result, accurate and individualized blood glucose regulation is hardly achieved. At present, in the field of diabetes treatment, it is generally believed that in vitro open-loop system composed of real-time continuous glucose monitoring system (CGMS) and CSII can help doctors to have an effective and dynamic clinical application experience to direct the regulation of the dosage of insulin pump for patients according to CGMS map, so as to achieve desired blood glucose control.

The real-time continuous glucose monitoring system, commonly known as CGMS, continuously records the glucose level in the intercellular fluid through an embedded subcutaneous glucose sensor, and then records the changes of blood glucose. Continuous blood glucose information obtained from CGMS can be used to map the blood glucose change, which facilitates clinical analysis and diagnosis and comprehensive identification of glucose fluctuation. It is, therefore, very important for blood glucose control and diabetes treatment.

Compared with the number of experienced and qualified physicians in China able to treat them, there is currently a disproportionately large number of diabetes patients. Therefore, it is necessary to use CGMS and CSII insulin pump system supported by artificial intelligence algorithm to assist doctors and patients to complete some simple medical decisions. For example, Chinese patent CN101254322A discloses a full-automatic intelligent infusion method and device for high-dose insulin based on model predictive control. With the support of real-time continuous glucose monitoring system (CGMS), a strong tracking filter is used online to detect diet and infuse initial high-dose insulin, so its main focus is pre-meal large dose. However, considering the risk of hypoglycemia, the automatically calculated high-dose insulin dose is likely to be unsafe for users.

Another example is Chinese patent CN103418053B. An individualized insulin injection pump system is described that uses the data of real-time continuous glucose monitoring system (CGMS) for modeling and simulation to assist in optimizing the basal infusion rate. The patented system, however, has no clinical significance for large dose insulin injection.

Another example, Chinese patent CN102500013A, discloses a portable intelligent insulin pump and its control model. This system dynamically monitors the user's blood glucose level to track the change of blood glucose and injects insulin to treat diabetes. This closed-loop infusion pump control model takes no account of the fact that patients may encounter dramatic blood glucose fluctuations after meals, and has a potential safety hazard. In addition, the inventions described above are each limited by the insufficient amount of reference data, and adopt the configuration regulation method at the current moment regardless of historical data. Therefore, the regulation results cannot reflect unique characteristics and courses of disease of individual patients themselves, and cannot be used to guide the medication after the removal of the insulin pump.

SUMMARY

The objective of the present invention is to provide a cloud big data-based system and method for individualized insulin pump configuration optimization, so as to overcome the deficiencies of the prior art.

The present invention adopts the following technical scheme.

A cloud big data-based system for insulin pump individualized configuration optimization includes an insulin pump, a real-time continuous glucose monitoring system, a smart phone, glucose monitoring application software installed in the smart phone and a cloud big data server.

The insulin pump includes a syringe pump body with a control module and a wireless transmission module, a replaceable drug container and a subcutaneous indwelling needle. The wireless transmission module of the insulin pump is wirelessly connected to the smart phone and a data transmission is performed between the wireless transmission module and the glucose monitoring application software.

The real-time continuous glucose monitoring system includes a replaceable implantable glucose sensor probe, a reusable signal collector and a signal transmitter. The signal transmitter of the real-time continuous glucose monitoring system is wirelessly connected to the smart phone and a data transmission is performed between the signal transmitter and the glucose monitoring application software.

The smart phone and the glucose monitoring application software installed in the smart phone have the function of data transmission with the real-time continuous glucose monitoring system through wireless transmission technique, and the function of data upload and download from the cloud big data server through smart phone data network or wireless network.

The cloud big data server has the functions of storing, updating, calculating and transmitting user's personal information and historical data.

The cloud big data server calculates the personalized parameters related to diabetes according to the stored user historical data, automatically corrects and calculates the parameter output data of insulin pump and implantable glucose sensor, and transfers it to the smart phone. The parameters include amount of carbohydrate converted by 1 unit of insulin CR, insulin sensitivity index IS, and insulin retention time TA, glucose release rate GR during fasting via metabolism, injection volume BOLUS of single high-dose injection, and basal infusion rate BASAL.

The insulin pump can download the latest user parameters from the cloud big data server through the smart phone, then calculate and recommend the high-dose insulin injection scheme according to the carbohydrate intake input by the user, and recommend the updated basal infusion rate scheme to the user according to the time segment of the user's basal infusion rate.

Further, the user's personal information and historical data stored in the cloud big data server include user's name, gender, age, contact number, serial number of insulin pump used, insulin pump infusion dose, infusion time and infusion rate records, blood glucose output value BG and corresponding data measurement time Ts, and carbohydrate intake, sleep and exercise recorded by individual patients.

Further, in the cloud big data server, the definition and calculation of physiological parameters CR, IS, TA, GR and insulin infusion volume are as follows:

CR: the amount of carbohydrate converted by one unit of insulin

IS: insulin sensitivity index

TA: insulin retention time

GR: the rate of glucose released into the blood by the body through metabolism during fasting BOLUS: injection volume of single high-dose injection BASAL: basal infusion rate, usually counted in insulin units per hour (U/h)

According to the given CR, IS, TA, the calculation formula for the BOLUS is as follows:

$$\text{BOLUS} = \frac{\text{CARBS}}{CR} + \frac{BGcurrent - BGtarget}{IS} - BOLUSprev\left(1 - \frac{\min(TI, TA)}{TA}\right)$$

Where, BGcurrent is the blood glucose value before high-dose injection read by CGMS; BGtarget is the target blood glucose value; BOLUSprev is the injection volume of the last high-dose injection; CARBS is the current carbohydrate intake input by the user; TI is the time between current high-dose injection and the midpoint of the previous high-dose injection process, min (TI, TA) is the smaller value of TI and TA, so that when TI is greater than or equal to TA, the residual amount of the previous high-dose injection $$BOLUSprev\left(1 - \frac{\min(TI, TA)}{TA}\right) \text{ is } 0.$$

According to the given GR, the BASAL during fasting for t is calculated as follows:

$$BASAL = \frac{\frac{BGstart - BGtarget + GR \times t}{IS} - BOLUSprev\left(1 - \frac{\min(TI, TA)}{TA}\right)}{t}$$

Where, BGstart is an average blood glucose after the fasting starts for a period of time read by CGMS, and TI is the time between current high-dose injection and the midpoint of the previous high-dose injection process.

Further, the cloud big data server can optimize the physiological parameters CR, IS, TA by collecting real-time data obtained by users using CGMS and insulin pump for high-dose injection. The specific steps are as follows:

Step A, establishing a regression equation $$BGbefore - BGafter = (BOLUS + BOLUSprev)IS + (-CARBS)\frac{IS}{CR} + (-BOLUSprev \times \min(TI, TA))\frac{IS}{TA}$$

where, BGbefore is the blood glucose value before high-dose injection, which is equal to BGcurrent in the calculation formula; BGafter is the measured blood glucose value after a period of high-dose injection.

Step B, obtaining the following data near the time Tstart at which each high-dose injection is performed from the insulin pump and CGMS through the smart phone:

Injection start time Tstart: insulin pump data
Injection end time Tend: insulin pump data
Injection volume BOLUS of high-dose injection at Tstart: insulin pump data
Blood glucose value BGbefore measured by implantable dynamic glucose sensor at Tstart
Blood glucose value BGafter measured by implantable dynamic glucose sensor after a period of Tend
Carbohydrate intake CARBS input by users near the Tstart
Forming a sample record packet for calculation $$[Tstart_n, Tend_n, BOLUS_n, CARBS_n, BGbefore_n, BGafter_n]$$

The data in the last three to six months are used for regression. The subscript number n of historical data variable is arranged in reverse order of Tstart, that is, the closer to the current historical data, the smaller the subscript number.

Step C, constructing a sample matrix:

$$G = \begin{bmatrix} \Delta BG_1 \\ \Delta BG_2 \\ \Delta BG_3 \\ \vdots \\ \Delta BG_n \end{bmatrix} \quad X = \begin{bmatrix} BOLUS'_1 & -CARBS_1 & -BOLUS_2 \times TI'_1 \\ BOLUS'_2 & -CARBS_2 & -BOLUS_3 \times TI'_2 \\ BOLUS'_3 & -CARBS_3 & -BOLUS_4 \times TI'_3 \\ \vdots & \vdots & \vdots \\ BOLUS'_n & -CARBS_n & -BOLUS_{n+1} \times TI'_n \end{bmatrix}$$

where, $\Delta BG_n = BGafter_n - BGbefore_n$, when $TI_n > TAu$, $BOLUS'_n = BOLUS_n + BOLUS_{n+1}$, $TI'_n = TI_n$, $TI_n = Tstart_n - (Tstart_{n+1} + Tend_{i+1})/2$;

when $TI_n > TAu$, $BOLUS'_n = BOLUS_n$, $TI'_n = 0$;
when $TAl \leq TI_n \leq TAu$, the sample was abandoned.
TAu is the upper limit allowed by TA, and TAl is the lower limit allowed by TA.

Step D, if for each n, $X_{n,3} = 0$, then:

$$X = \begin{bmatrix} BOLUS'_1 & -CARBS_1 \\ BOLUS'_2 & -CARBS_2 \\ BOLUS'_3 & -CARBS_3 \\ \vdots & \vdots \\ BOLUS'_n & -CARBS_n \end{bmatrix} \quad C = \begin{bmatrix} IS \\ IS/CR \end{bmatrix}$$

Otherwise, the sample matrix remains unchanged.

Step E, solving the overdetermined equation G=XC, the weighted least square method is used to solve:
$\hat{C} = (X^T W X)^{-1} X^T W G$.

Step F, eliminating the abnormal data: calculate the residual error: $\hat{\varepsilon} = G - X\hat{C}$, eliminate the data items whose residual error is greater than the threshold, and then repeat the regression algorithm A-F until there are no data items whose residual error is greater than the threshold.

Step G, calculating the updated physiological parameters IS, CR, TA according to the results of the regression algorithm:

$\hat{IS} = \hat{C}_{1,1}$ $\hat{CR} = \hat{C}_{1,1}/\hat{C}_{2,1}$

If $\hat{C}_{2,1}$ exists, the $\hat{TA} = \hat{C}_{1,1}/\hat{C}_{2,1}$, otherwise $\hat{TA} = TA$.

Step H, finally, using the obtained $\hat{IS}$, $\hat{CR}$ and $\hat{TA}$ to correct the currently set IS, CR and TA with a certain correction ratio γ, wherein the range of γ values is 0<γ<1, $IS := (1-\gamma) \times IS + \gamma \times \hat{IS}$ $CR := (1-\gamma) \times CR + \gamma \times \hat{CR}$ $TA := (1-\gamma) \times TA + \gamma \times TA \times \hat{TA}$ the above is used as setting parameters for high-dose injection of insulin pump from now on;
TAl and TAu are revised at the same time:

$TAl = TA \times \tau\%$, where $0 < \tau < 100$;

$TAu := TA \times \upsilon\%$, where $100 < \upsilon < 150$;

the physiological parameters IS, CR, TA, TA and TAu are stored and updated to the cloud big data server and transferred to the mobile application and insulin pump.

Further, the cloud big data server can optimize the value of the physiological parameter GR in different time periods and the corresponding basal infusion rate BASAL by collecting real-time data obtained by users using CGMS and insulin pump in real time. The specific steps are as follows:

Step A, first, segmenting the 24 hours a day according to the basal infusion rate established by the user with reference to the doctor's recommendations and their own situation. The GR and BASAL values in each time period need to be set and calculated independently. For each time period and 2 hours before each time period, if the user eats something, and a high-dose injection accompanied with or without eating is performed, the data obtained at 2 hours after the meal or the high-dose injection needs to be excluded from this time period. The data of the time period is updated to only include the data of the longer continuous time remaining after the removal of the data at 2 hours after the meal or the high-dose injection;

Step B, collecting sample data in each valid time period:
Tstart: the start time of the time period
BGstart: the average value of blood glucose in the previous short period of the time period
BGend: the average value of blood glucose in the last short period of the time period BASAL: basal infusion rate during this time period
t: duration of this time period
IS: insulin sensitivity index
TA: insulin retention time $$RESIDUAL = BOLUSprev\left(1 - \frac{\min(TI, TA)}{TA}\right);$$

residual insulin in the body at the beginning of the time period

SNR: signal-to-noise ratio of dynamic blood glucose data

Forming a sample record package for calculation

[$Tstart_n, BGstart_n, BGend_n, BASAL_n, t_n, RESIDUAL_n,$ $SNR_n$] and system parameters $IS$ and $TA$;

The data of the same time period in the last three to six months are used for regression, and the subscript number n of historical data variables is arranged in reverse order of Tstart, that is, the closer the current historical data is, the smaller the subscript number is.

Step C, for each effective time period, considering the effectiveness of ingesting insulin, during which the body releases total glucose ΔBG into the blood through metabolism:

$$\Delta BG_n = BGend_n - BGstart_n + [BASAL_n \times t_n + RESIDUAL_n] \times IS$$

establishing the regression equation $\Delta BG = GR \times \tau$;

Step D, for each valued time period, using the regression method to calculate the updated value $\widetilde{GR}$ of GR $$\widetilde{GR} = \frac{\sum_{n=1}^{N} t_n \times \Delta BG_n \times SNR_n \times w(T'_n)}{\sum_{n=1}^{N} t_n^2 \times SNR_n \times w(T'_n)}$$

where, w(T') is the time-related weight, $T'_n = Tcurrent - Tstart_n$, Tcurrent is the current time, that is, the time of the latest historical data $Tstart_1$;

The closer to the nearest sample, the greater the weight;

Step E, using the obtained $\widetilde{GR}$ to correct the currently set GR with a certain correction ratio γ

$$GR := (1-\gamma) \times GR + \gamma \times \widetilde{GR}$$

The range of γ values is 0<γ<1;

Step F, using the modified GR and the historical sample packet (BGstart$_n$, t$_n$, RESIDUAL$_n$] of the same time period to calculate the value $\widetilde{BASAL}$ that should be set in this time period after correction according to the formula:

$$\widetilde{BASAL}'_n = \frac{\frac{BGstart_n - BGtarget + GR \times t_n}{IS} - RESIDUAL_n}{t_n};$$

Step G, weighting all the calculated $\widetilde{BASAL}$ in time to calculate the current BASAL correction value $\widetilde{BASAL}$:

$$\widetilde{BASAL} = \frac{\sum_{n=1}^{N} \widetilde{BASAL}'_n \times w'(T'_n)}{\sum_{n=1}^{N} w'(T'_n)}$$

where, w(T') is the time-related weight, and the closer the sample is to the current time, the greater the weight is;

Step H, if the difference between the calculated value $\widetilde{BASAL}$ and the current BASAL value exceeds the threshold, using the obtained $\widetilde{BASAL}$ to correct the currently set BASAL with a certain correction ratio γ:

$$BASAL := (1-\gamma) \times BASAL + \gamma \times \widetilde{BASAL}$$

The range of γ values is 0<γ<1;

BASAL is stored and updated as the setting parameter of the basal injection rate of the insulin pump, stored with the physiological parameter GR in the cloud big data server and transferred to the mobile application and the insulin pump.

Further, the cloud big data server can optimize the basal infusion rate BASAL in different time periods by collecting real-time data obtained by users using CGMS and insulin pump in real time. Other specific steps are as follows:

Step A, first, segmenting the 24 hours a day according to the basal infusion rate established by the user with reference to the doctor's recommendations and his/her own situation. The BASAL value in each time period needs to be set and calculated independently. For each time period and 2 hours before the each time period, if the user eats, and a high-dose injection accompanied with or without food is performed, the data obtained at 2 hours after the meal or high-dose injection needs to be excluded from this time period. The data in this time period is updated to include only the data of the long continuous time remaining after the removal of the data obtained at 2 hours after the eating/high-dose injection from the time period;

Step B, collecting sample data in each valid time period:
Tstart: the start time of the time period
BGstart: the average value of blood glucose in the previous short period of the time period
BGend: the average value of blood glucose in the last short period of the time period
BASAL: basal infusion rate during this time period
t: duration of this time period
IS: insulin sensitivity index
TA: insulin retention time $$RESIDUAL = BOLUSprev\left(1 - \frac{\min(TI, TA)}{TA}\right);$$

residual insulin in the body at the beginning of the time period

Forming a sample record package for calculation

[$Tstart_n, BGstart_n, BGend_n, BASAL_n, t_n, RESIDUAL_n$] and system parameters $IS$ and $TA$;

The data of the same time period in the last three to six months are used for regression, and the subscript number n of historical data variables is arranged in reverse order of Tstart, that is, the closer the current historical data is, the smaller the subscript number.

Step C, for the n$^{th}$ time period, using the historical sample packet of the n$^{th}$ time period and calculating value $\widetilde{BASAL}$ that should be set in this time period after correction according to the formula:

$$\widetilde{BASAL}'_n = BASAL_n + \frac{RESIDUAL_n}{t_n} - \frac{BGtraget - BGend_n}{IS \times t_n}$$

Step D, weighting all the calculated $\widetilde{BASAL}$ in time to calculate the current BASAL correction value $\widetilde{BASAL}$:

$$\widetilde{BASAL} = \frac{\sum_{n=1}^{N} \widetilde{BASAL}'_n \times w'(T'_n)}{\sum_{n=1}^{N} w'(T'_n)}$$

where, $w'(T')$ is the time-related weight, and the closer the sample is to the current time, the greater the weight is;

Step E, if the difference between the calculated value $\widetilde{BASAL}$ and the current BASAL value exceeds the threshold, using the obtained $\widetilde{BASAL}$ to correct the currently set BASAL with a certain correction ratio $\gamma$:

$$BASAL := (1-\gamma) \times BASAL + \gamma \times \widetilde{BASAL}$$

The range of $\gamma$ values is $0 < \gamma < 1$.

A cloud big data-based method for insulin pump individualized configuration optimization includes the following steps:

Step 1, obtaining, by a smart phone application, cloud big data server data when the system is started to determine whether a user is using the insulin injection system for the first time, if yes, prompting the user to set the parameters IS, CR, TA, GR, time segmentation and the basal injection rate or to continue to use a default setting, if no, downloading the updated above parameters from a cloud big data server;

Step 2, entering a high-dose injection mode if the user inputs a high-dose injection command manually, otherwise the insulin pump maintains in a basic injection mode;

Step 3, in the basic injection mode, performing an insulin injection according to the preset basic rate of the current time period, and uploading blood glucose data monitored by CGMS to the cloud server on a regular basis, checking whether there is an update of the GR and basic rate of the cloud big data server after the end of this time period or after the operation of the insulin pump, if yes, updating local storage parameters, and then repeating step 2, if no, repeating step 2 directly;

Step 4, in the high-dose mode, the insulin pump prompting the user to manually input a carbohydrate intake CARBS and confirm a target blood glucose value to be achieved through the smart phone application, while obtaining the current blood glucose value BGcurrent measured by CGMS;

Step 5, calculating a required high-dose injection volume using the previously set or obtained parameter values:

$$BOLUS = CARBS/CR + (BGcurrent - BGtarget)/IS - BOLUSprev[1 - \min(TI, TA)/TA];$$

Step 6, prompting the patient to confirm the infusion volume and high-dose infusion time, and calculating an injection stop time $Tend = Tstart + T_{BOLUS}$, wherein $T_{BOLUS}$ = infusion volume/bolus-rate, bolus-rate is a user-defined high-dose infusion rate of insulin;

Step 7, uploading insulin injection information Tstart, Tend, BOLUS, CARBS and CGMS blood glucose monitoring data to the cloud big data server;

Step 8, performing the high-dose injection until the Tend is reached;

Step 9, detecting whether there are physiological parameters updated in the cloud, if yes, updating the local storage parameters, and then repeating step 2; if no, repeating step 2 directly.

The advantages of the present invention are as follows:

1. The present invention provides an individualized configuration optimization system of an insulin pump, which includes a smart phone, a cloud big data server, a real-time continuous glucose monitoring system and an insulin pump. The present invention also establishes a set of algorithms, which establishes a regression equation between the historical data of blood glucose fluctuations, carbohydrate intake and insulin injection records, calculates the user's physiological parameters related to diabetes and corrects these parameters in real time according to the updated data and recalculates the required insulin injection rate. Because the physiological characteristics and course of disease of each diabetic patient are different, and the individual difference is significant, the insulin injection mode that each person needs is also very different. The system constructed by the present invention can effectively calculate the individual optimal insulin injection volume and injection rate of each user through the historical data of blood glucose measurement of individual users stored in the cloud, so as to assist doctors and patients in making more effective individualized treatment plans for diabetes.

2. The present invention realizes that the settings of the insulin pump are automatically updated in real time according to the user's historical data, so that the user can timely understand his/her own condition, complete the adjustment of the diabetes treatment plan and provide real-time feedback information without registering for medical treatment. As a result, the present invention alleviates the psychological anxiety of patients with poor control of the disease and the life burden of the need to manage the pump settings in time, and at the same time saves the time and cost of frequent medical consultations by patients.

3. The cloud big data server of the present invention can archive the individualized parameters related to diabetes and blood glucose historical data of the user, and the historical data of insulin infusion and form an analysis report for the doctor's reference, so as to make the continued treatment plan after the patient stops the insulin pump therapy.

DETAILED DESCRIPTION OF THE EMBODIMENTS

The present invention is described in more detail below in combination with embodiments and drawings. The following embodiments are used only to illustrate the present invention, but are not intended to limit the scope of implementation of the present invention.

Figure 1:
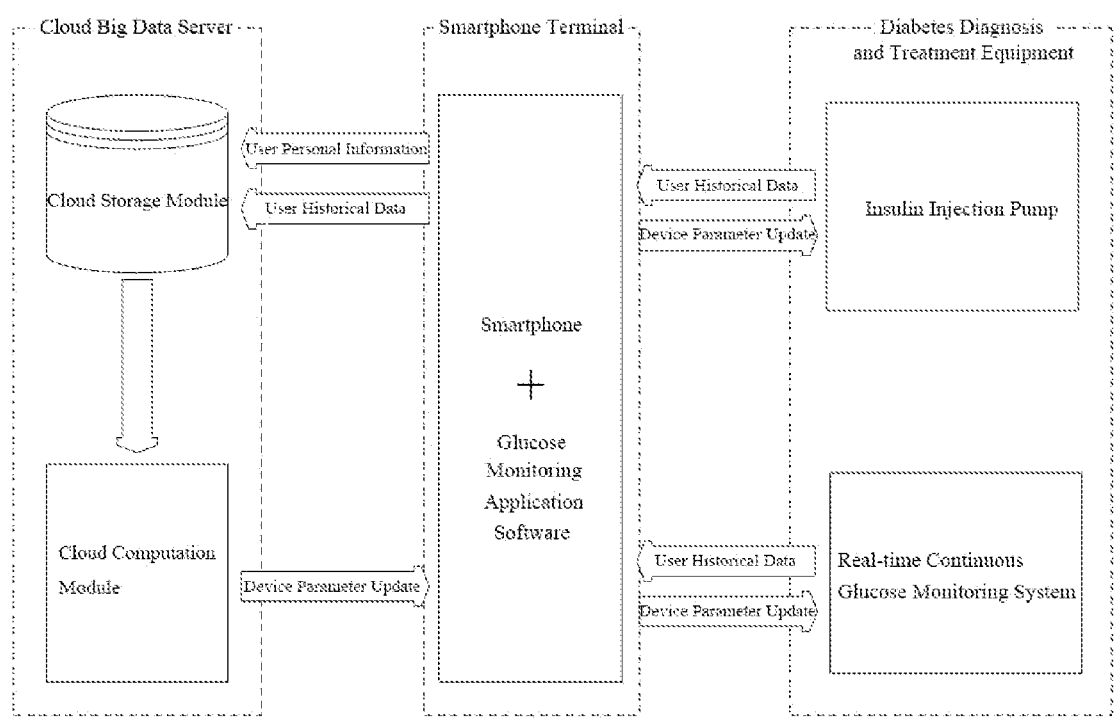
FIG. 1 is a schematic diagram showing a structure of the system the present invention.

A cloud big data-based system for insulin pump individualized configuration optimization, as shown in FIG. 1, includes an insulin pump, a real-time continuous glucose monitoring system (CGMS), a smart phone, a glucose monitoring application software installed in the smart phone and a cloud big data server.

The insulin pump includes a syringe pump body with a control module and a wireless transmission module, a replaceable drug container and a subcutaneous indwelling needle. The wireless transmission module of the insulin pump is wirelessly connected to the smart phone via Bluetooth and transmits data with the glucose monitoring application software. During the connection and data transmission between the smart phone and the insulin pump, it can also be that the insulin pump only transmits insulin injection records and time information to the smart phone glucose monitoring application software and executes the high-dose and basal infusion rate commands issued by the glucose monitoring application software. The BOLUS and BASAL are calculated in the smart phone glucose monitoring application software according to the following algorithm, and the storage and cloud data synchronization and update of the relevant parameters IS, CR, TA and GR are also realized in the smart phone glucose monitoring application software, that is, the smart phone glucose monitoring application software replaces the control module of the insulin pump to process the data.

The real-time continuous glucose monitoring system includes a replaceable implantable glucose sensor probe, a reusable signal collector and a signal transmitter. The signal transmitter of the real-time continuous glucose monitoring system is connected to the smart phone through wireless means such as Bluetooth communication and transmits data with the glucose monitoring application software.

The smart phone and the glucose monitoring application software installed in the smart phone have the function of data transmission with the real-time continuous glucose monitoring system and the insulin pump through wireless transmission technology such as Bluetooth, and the function of data upload and download through smart phone data network or wireless network from the cloud big data server. The smart phone can also be other smart devices.

The cloud big data server has the functions of storing, updating, calculating and transmitting user's personal information and historical data. The user's personal information and historical data stored in the cloud big data server include but are not limited to the user's name, gender, age, contact number, serial number of insulin pump products used, records of insulin pump infusion volume, infusion time and infusion rate, blood glucose output value BG and corresponding data measurement time Ts, carbohydrate intake, sleep and exercise recorded by the patient.

The cloud big data server calculates the personalized parameters related to diabetes according to the stored user historical data, and automatically corrects and calculates the parameter output data of insulin pump and implantable glucose sensor and transfers it to the smart phone. The parameters include, but are not limited to, the amount CR of carbohydrate converted by 1 unit of insulin, insulin sensitivity index IS, and insulin retention time TA, glucose release rate GR via metabolism during fasting, injection volume BOLUS of single high-dose injection and basal infusion rate BASAL.

The insulin pump can download the latest user parameters from the cloud big data server through the smart phone, then calculate and recommend the high-dose insulin injection scheme according to the carbohydrate intake input by the user, and recommend the updated basal infusion rate scheme to the user according to the time segmentation of the user's basal infusion rate.

The cloud big data server can archive the individualized parameters related to diabetes and blood glucose historical data of the user, and the historical data of insulin infusion and form an analysis report for the doctor's reference, so as to make the continued treatment plan after the patient stops the insulin pump therapy.

In the cloud big data server, the definition and calculation of the physiological parameters CR, IS, TA, GR and insulin infusion volume are as follows:

CR: Carbohydrate Ratio, the amount of carbohydrate converted by one unit of insulin IS: insulin sensitivity, insulin sensitivity index TA: active insulin time, insulin retention time GR: Glucose Release Rate, the rate of glucose released into the blood by the body through metabolism during fasting BOLUS: injection volume of single large-dose injection BASAL: basal infusion rate, usually counted in insulin units per hour (U/h)

According to the given CR, IS, TA, the BOLUS calculation formula is as follows:

$$BOLUS = \frac{CARBS}{CR} + \frac{BGcurrent - BGtarget}{IS} - BOLUSprev\left(1 - \frac{\min(TI, TA)}{TA}\right)$$

where, BGcurrent is the blood glucose value before the high-dose injection read by CGMS; BGtarget is the target blood glucose value; BOLUSprev is the injection volume of the previous high-dose injection; CARBS is the current carbohydrate intake input by the user; TI is the time between current high-dose injection and the midpoint of the previous high-dose injection process, min (TI, TA) is the smaller value of TI and TA, so that when TI is greater than or equal to TA, the residual amount of the previous high-dose injection $$BOLUSprev\left(1 - \frac{\min(TI, TA)}{TA}\right) \text{ is } 0;$$

According to the given GR, the BASAL during fasting for t is calculated as follows:

$$BASAL = \frac{\frac{BGstart - BGtarget + GR \times t}{IS} - BOLUSprev\left(1 - \frac{\min(TI, TA)}{TA}\right)}{t}$$

Where BGstart is the average blood glucose in a period after the fasting starts read by CGMS, and TI is the time between current high-dose injection and the midpoint of the previous high-dose injection process.

The cloud big data server can optimize the physiological parameters CR, IS, and TA by collecting real-time data obtained by users using CGMS and insulin pump for high-dose injection. The specific steps are as follows:

Step A, establishing a regression equation $$BGbefore - BGafter = (BOLUS + BOLUSprev)IS +$$
$$(-CARBS)\frac{IS}{CR} + (-BOLUSprev \times \min(TI, TA))\frac{IS}{TA}$$

where, BGbefore is the blood glucose value before the high-dose injection, which is the equal to the BGcurrent in the calculation formula; BGafter is the measured blood glucose value after a period of high-dose injection, such as after 2 hours of the high-dose injection;

Step B, obtaining the following data near each high-dose injection Tstart from the insulin pump and CGMS through the smart phone:

Injection start time Tstart: insulin pump data

Injection end time Tend: insulin pump data

Injection volume BOLUS of high-dose injection at Tstart: insulin pump data

Blood glucose value BGbefore measured by implantable dynamic glucose sensor at Tstart Blood glucose value BGafter measured by implantable dynamic glucose sensor a period after Tend (for example, 2 hours after Tend)

Carbohydrate intake CARBS input by users near Tstart

Forming a sample record packet for calculation $$[Tstart_n, Tend_n, BOLUS_n, CARBS_n, BGbefore_n, BGafter_n]$$

The data in the last three to six months are used for regression. The subscript number n of historical data variable is arranged in reverse order of Tstart, that is, the closer to the current historical data, the smaller the subscript number;

Step C, constructing the sample matrix:

$$G = \begin{bmatrix} \Delta BG_1 \\ \Delta BG_2 \\ \Delta BG_3 \\ \vdots \\ \Delta BG_n \end{bmatrix}$$

$$X = \begin{bmatrix} BOLUS'_1 & -CARBS_1 & -BOLUS_2 \times TI'_1 \\ BOLUS'_2 & -CARBS_2 & -BOLUS_3 \times TI'_2 \\ BOLUS'_3 & -CARBS_3 & -BOLUS_4 \times TI'_3 \\ \vdots & \vdots & \vdots \\ BOLUS'_n & -CARBS_n & -BOLUS_{n+1} \times TI'_n \end{bmatrix}$$

where, $\Delta BG_n = BG\text{after}_n - BG\text{before}_n$

When $TI_n < TAl$, $BOLUS'_n = BOLUS_n + BOLUS_{n+1}$, $TI'_n = TI_n$, $TI_n = T\text{start}_n - (T\text{start}_{n+1} + T\text{end}_{n+1})/2$;

When $TI_n > TAu$, $BOLUS'_n = BOLUS_n$, $TI'_n = 0$;
When $TAl \leq TI_n \leq TAu$, the sample was abandoned.

TAu is the upper limit allowed by TA, and TAl is the lower limit allowed by TA.

Step D, if for each n, $X_{n,3} = 0$, then:

$$X = \begin{bmatrix} BOLUS'_1 & -CARBS_1 \\ BOLUS'_2 & -CARBS_2 \\ BOLUS'_3 & -CARBS_3 \\ \vdots & \vdots \\ BOLUS'_n & -CARBS_n \end{bmatrix}$$

$$C = \begin{bmatrix} IS \\ IS/CR \end{bmatrix}$$

Otherwise, the sample matrix remains unchanged;

Step E, solving the overdetermined equation G=XC,

The weighted least square method is used to solve: $\hat{C} = (X^T W X)^{-1} X^T W G$;

Step F, eliminating the abnormal data: calculate the residual error: $\hat{\varepsilon} = G - X\hat{C}$, eliminate the data items whose residual error is greater than the threshold, and then repeat the regression algorithm A-F until there are no data items whose residual error is greater than the threshold.

Step G, calculating the updated physiological parameters IS, CR, and TA according to the results of the regression algorithm:

$\hat{IS} = \hat{C}_{1,1}$ $\hat{CR} = \hat{C}_{1,1}/\hat{C}_{2,1}$

If $\hat{C}_{3,1}$ exists, then $\hat{TA} = \hat{C}_{1,1}/\hat{C}_{3,1}$, otherwise $\hat{TA} = TA$;

Step H, finally, using the obtained $\hat{IS}$, $\hat{CR}$ and $\hat{TA}$ to correct the currently set IS, CR and TA with a certain correction ratio $\gamma$, wherein the range of $\gamma$ values is $0 < \gamma < 1$, $IS := (1-\gamma) \times IS + \gamma \times \hat{IS}$ $CR := (1-\gamma) \times CR + \gamma \times \hat{CR}$ $TA := (1-\gamma) \times TA + \gamma \times \hat{TA}$ the above is used as a setting parameter for high-dose injection of insulin pump from now on;

TAl and TAu are revised at the same time:

$TAl := TA \times \tau\%$, wherein $0 < \tau < 100$;

$TAu := TA \times \upsilon\%$, wherein $100 < \upsilon < 150$;

Storing and updating physiological parameters IS, CR, TA, TAl and TAu to the cloud big data server and pushing them to mobile application and insulin pump.

The cloud big data server can optimize the value of physiological parameter GR in different time periods and the corresponding basal infusion rate BASAL by collecting real-time data obtained by users using CGMS and insulin pump in real time. The specific steps are as follows:

Step A, first, segmenting the 24 hours a day according to the basal infusion rate established by the user with reference to the doctor's recommendations and their own situation. The GR and BASAL values in each time period need to be set and calculated independently. For each time period and 2 hours before the each time period, if the user eats something, and a high-dose injection accompanied with or without food is performed, the data obtained at 2 hours after the meal or the high-dose injection needs to be excluded from this time period, the data of the time period is updated to only include the data of the longer continuous time remaining after the removal of the data obtained at 2 hours after the meal/high-dose injection. For example, if the time period is set to: (1) 6:00-13:00, (2) 13:00-20:00, (3) 20:00—the next day 6:00, and the user eats and injects insulin at 7:00, 12:00, 18:00, then the time period (1) is adjusted to 9:00-12:00, the time period (2) is adjusted to 14:00-18:00, and the time period (3) remains unchanged.

Step B, collecting sample data in each valid time period:
Tstart: the start time of the time period
BGstart: the average value of blood glucose in the previous short period (for example, 15 min) of the time period
BGend: the average value of blood glucose in the last short period (for example, 15 min) of the time period
BASAL: basal infusion rate during this time period
t: duration of this time period
IS: insulin sensitivity index
TA: insulin retention time $$RESIDUAL = BOLUSprev\left(1 - \frac{\min(TI, TA)}{TA}\right);$$

residual insulin in the body at the beginning of the time period
SNR: signal-to-noise ratio of dynamic blood glucose data
Forming a sample record package for calculation

[$T\text{start}_n, BG\text{start}_n, BG\text{end}_n, BASAL_n, t_n, RESIDUAL_n, SNR_n$] and system parameters $IS$ and $TA$;

The data of the same period in the last three to six months are used for regression, and the subscript number n of historical data variables is arranged in reverse order of Tstart, that is, the closer to the current historical data, the smaller the subscript number.

Step C, for each effective time period, considering the effectiveness of ingesting insulin, during which the body releases total glucose $\Delta BG$ into the blood through metabolism:

$\Delta BG_n = BG\text{end}_n - BG\text{start}_n + [BASAL_n \times t_n + RESIDUAL_n] \times IS$ establishing regression equation $\Delta BG = GR \times t$;

Step D, for each valid time period, using the regression method to calculate the updated value $\widetilde{GR}$ of GR $$\widetilde{GR} = \frac{\sum_{n=1}^{N} t_n \times \Delta BG_n \times SNR_n \times w(T'_n)}{\sum_{n=1}^{N} t_n^2 \times SNR_n \times w(T'_n)}$$

where, w(T') is the time-related weight, $T'_n$=Tcurrent–$Tstart_1$, $Tcurrent_n$ is the current time, that is, the time of the latest historical data $Tstart_1$;

The closer to the nearest sample, the greater the weight; for example, $$w = \begin{cases} 0.6 & T' \leq 1 \text{ month} \\ 0.3 & 1 \text{ month} < T' \leq 2 \text{ months} \\ 0.1 & 2 \text{ months} < T' \leq 3 \text{ months} \end{cases}$$

Step E, using the obtained $\widetilde{GR}$ to correct the currently set GR with a certain correction ratio γ

$$GR := (1-\gamma) \times GR + \gamma \times \widetilde{GR}$$

The range of γ values is 0<γ<1;

Step F, using the modified GR and the historical sample packet [$BGstart_n$, $t_n$, $RESIDUAL_n$] of the time period to calculate value $\widetilde{BASAL}$ that should be set in this time period after correction according to the formula:

$$\widetilde{BASAL}'_n = \frac{\frac{BGstart_n - BGtarget + GR \times t_n}{t_n} - RESIDUAL_n}{t_n}$$

Step G, weighting all the calculated $\widetilde{BASAL}'$ in time to calculate the current BASAL correction value $\widetilde{BASAL}$:

$$\widetilde{BASAL} = \frac{\sum_{n=1}^{N} \widetilde{BASAL}'_n \times w'(T'_n)}{\sum_{n=1}^{N} w'(T'_n)}$$

where, w(T') is the time-related weight, and the closer the sample is to the current time, the greater the weight is;

For example: $w' = \begin{cases} 0.6 & T' \leq 1 \text{ month} \\ 0.3 & 1 \text{ month} < T' \leq 2 \text{ months} \\ 0.1 & 2 \text{ months} < T' \leq 3 \text{ months} \end{cases}$ Step H, if the difference between the calculated value $\widetilde{BASAL}$ and the current BASAL value exceeds the threshold, using the obtained $\widetilde{BASAL}$ to correct the currently set BASAL with a certain correction ratio γ:

$$BASAL := (1-\gamma) \times BASAL + \gamma \times \widetilde{BASAL}$$

The range of γ values is 0<γ<1;

Storing and updating BASAL as the setting parameter of the basal injection rate of the insulin pump, and storing it to the cloud big data server together with the physiological parameter GR and transfer it to the mobile application and the insulin pump.

The cloud big data server can optimize the basal infusion rate BASAL in different time periods by collecting real-time data obtained by users using CGMS and insulin pump in real time. Other specific steps are as follows:

Step A, first, segmenting the 24 hours a day according to the basal infusion rate established by the user with reference to the doctor's recommendations and his/her own situation. The BASAL value in each time period needs to be set and calculated independently. For each time period and 2 hours before the each time period, if the user eats something, and a high-dose injection accompanied with or without food is performed, the data obtained at 2 hours after the meal or high-dose injection needs to be excluded from this time period, the data in this time period is updated to include only the data of the long continuous time remaining after the removal of the data obtained at 2 hours after the eating/high-dose injection; Step B, collecting sample data in each valid time period:

Tstart: the start time of the time period

BGstart: the average value of blood glucose in the previous short period of the time period BGend: the average value of blood glucose in the last short period of the time period BASAL: basal infusion rate during this time period t: duration of this time period IS: insulin sensitivity index TA: insulin retention time $$RESIDUAL = BOLUSprev\left(1 - \frac{\min(TI, TA)}{TA}\right):$$

residual insulin in the body at the beginning of the time period

Forming a sample record package for calculation

[$Tstat_n$, $BGstat_n$, $BGend_n$, $BASAL_n$, $t_n$, $RESIDUAL_n$] and system parameters IS and TA;

The data of the same period in the last three to six months are used for regression, and the subscript number n of historical data variables is arranged in reverse order of Tstart, that is, the closer to the current historical data, the smaller the subscript number.

Step C, for the $n^{th}$ time period, using the historical sample packet of the $n^{th}$ time period to calculate value $\widetilde{BASAL}$ that should be set in this time period after correction according to the formula:

$$\widetilde{BASAL}'_n = BASAL_n + \frac{RESIDUAL_n}{t_n} - \frac{BGtarget - BGend_n}{IS \times t_n}$$

Step D, weighting all the calculated $\widetilde{BASAL}$, in time to calculate the current BASAL correction value BA: $\widetilde{BASAL}$ $$\widetilde{BASAL} = \frac{\sum_{n=1}^{N} \widetilde{BASAL}'_n \times w'(T'_n)}{\sum_{n=1}^{N} w'(T'_n)}$$

where, w'(T') is the time-related weight, and the closer the sample is to the current time, the greater the weight is;

Step E, if the difference between the calculated value $\widetilde{BASAL}$ and the current BASAL value exceeds the threshold, using the obtained $\widetilde{BASAL}$ to correct the currently set BASAL with a certain correction ratio γ:

$$BASAL := (1-\gamma) \times BASAL + \gamma \times \widetilde{BASAL}$$

The range of γ values is 0<γ<1.

Figure 2:
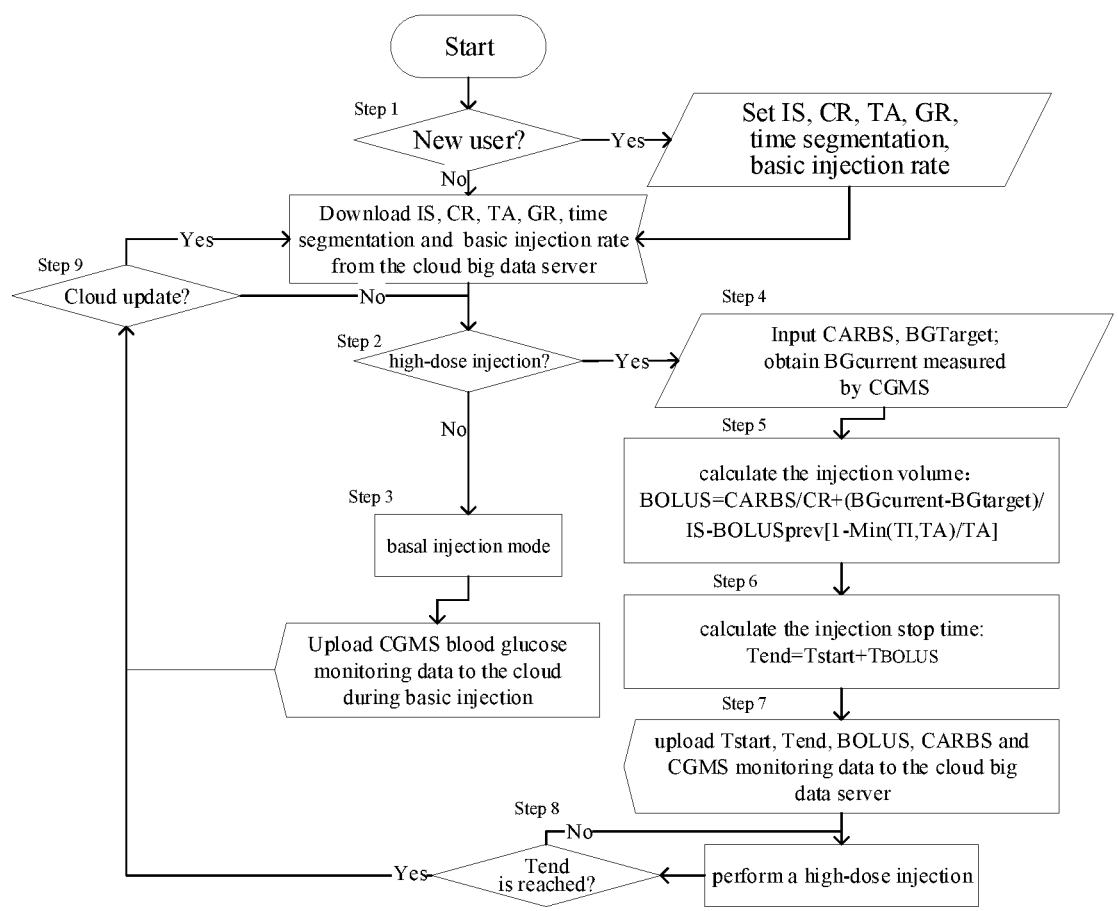
FIG. 2 is a flow chart of the method of the present invention.

A cloud big data-based method for insulin pump individualized configuration optimization, as shown in FIG. 2, includes the following steps:

Step 1, when the system is started, the smart phone application obtains the cloud big data server data to determine whether the user is using the insulin injection system for the first time. If yes, the user is prompted to set the parameters IS, CR, TA, GR, time segmentation and the basal injection rate or to continue to use the default setting. If no, the updated above parameters are downloaded from the cloud big data server.

Step 2, if the user inputs the high-dose injection command manually, the insulin pump enters the high-dose mode. Otherwise, the insulin pump maintains in the basic injection mode.

Step 3, in the basic injection mode, insulin injection is performed according to the preset basic rate of the current time period, and the blood glucose data monitored by CGMS are uploaded to the cloud server on a regular basis. After the end of this time period or after the operation of the insulin pump, checking whether there is an update of the GR and basic rate of the cloud big data server. If yes, updating the local storage parameters, and then repeating step 2. If no, repeating step 2 directly.

Step 4, in the high-dose mode, the insulin pump prompts the user to manually enter the carbohydrate intake CARBS and confirm the target blood glucose value to be achieved through the smart phone application, while obtaining the current blood glucose value BGcurrent measured by CGMS.

Step 5, the required high-dose injection volume is calculated using the previously set or obtained parameter values:

BOLUS=CARBS/*CR*+(*BG*current−*BG*target)/*IS*−BOLUSprev[1−min(*TI,TA*)/*TA*];

Step 6, the patient is prompted to confirm the infusion volume and high-dose infusion time, and the injection stop time is calculated as Tend=Tstart+T$_{BOLUS}$, where =infusion volume/bolus-rate. Bolus-rate is the user-defined high-dose insulin infusion rate.

Step 7, the insulin injection information Tstart, Tend, BOLUS, CARBS and CGMS blood glucose monitoring data are uploaded to the cloud big data server.

Step 8, the high-dose injection is performed until the Tend is reached.

Step 9, detecting whether there are physiological parameters updated in the cloud. If yes, updating the local storage parameters, and then repeating step 2. If no, repeating step 2 directly.

What is claimed is:

1. A cloud big data-based system for insulin pump individualized configuration optimization, comprising an insulin pump, a real-time continuous glucose monitoring system (CGMS), a smart phone, a glucose monitoring application software installed in the smart phone, and a cloud big data server; wherein the insulin pump comprises a syringe pump body with a control module and a wireless transmission module, a replaceable drug container and a subcutaneous indwelling needle; the wireless transmission module of the insulin pump is wirelessly connected to the smart phone and transmits data with the glucose monitoring application software;

the real-time continuous glucose monitoring system comprises a replaceable implantable glucose sensor probe, a reusable signal collector and a signal transmitter; the signal transmitter of the real-time continuous glucose monitoring system is wirelessly connected to the smart phone and transmits data with the glucose monitoring application software;

the smart phone and the glucose monitoring application software installed in the smart phone have a function of data transmission with the real-time continuous glucose monitoring system and the insulin pump through a wireless transmission technique, and a function of data upload and download through a smart phone data network or a wireless network from the cloud big data server;

the cloud big data server has functions of storing, updating, calculating and transmitting user's personal information and user's historical data;

the cloud big data server calculates user's personalized parameters related to diabetes according to the user's historical data stored in the cloud big data server to obtain calculated user's personalized parameters, and automatically corrects and calculates a parameter output data of the insulin pump and an implantable glucose sensor to obtain a corrected and calculated parameter output data, and transfers the calculated user's personalized parameters and the corrected and calculated parameter output data to the smart phone, the calculated user's personalized parameters and the corrected and calculated parameter output data comprise an amount CR of carbohydrate converted by 1 unit of insulin, an insulin sensitivity index IS, insulin retention time TA, a glucose release rate GR during fasting via metabolism, an injection volume BOLUS of a single high-dose injection and a basal infusion rate BASAL;

the insulin pump downloads the calculated user's personalized parameters and the corrected and calculated parameter output data from the cloud big data server through the smart phone, then calculates and recommends a high-dose insulin injection scheme according to a carbohydrate intake input by the user, and recommends an updated basal infusion rate scheme to the user according to a time segmentation of the basal infusion rate, wherein a definition and a calculation method of the CR, the IS, the TA, the GR and an insulin infusion volume implemented in the cloud big data server includes the following:

CR: the amount of carbohydrate converted by 1 unit of insulin,

IS: the insulin sensitivity index,

TA: the insulin retention time,

GR: the glucose release rate during fasting via metabolism,

BOLUS: the injection volume of the single high-dose injection,

BASAL: the basal infusion rate, wherein the BASAL is counted in insulin units per hour (U/h), and according to the CR, IS, TA, calculating the BOLUS is as follows:

$$BOLUS = \frac{CARBS}{CR} + \frac{BGcurrent - BGtarget}{IS} - BOLUSprev\left(1 - \frac{\min(TI, TA)}{TA}\right)$$

wherein, BGcurrent is a blood glucose value before a high-dose injection read by the real-time CGMS; BGtarget is a target blood glucose value; BOLUSprev is an injection volume of a previous high-dose injection; CARBS is a current carbohydrate intake input by the user; TI is a time between a current high-dose injection and a midpoint of the previous high-dose injection, min (TI, TA) is a smaller value of the TI and the TA, so that when the TI is greater than or equal to the TA, a residual amount of the previous high-dose injection $$BOLUSprev\left(1 - \frac{\min(TI, TA)}{TA}\right) \text{ is } 0,$$

and
according to the GR, calculating the BASAL during a fasting period (t) as follows:

$$BASAL = \frac{\frac{BGstart - BGtarget + GR \times t}{IS} - BOLUSprev\left(1 - \frac{\min(TI, TA)}{TA}\right)}{t}$$

wherein, BGstart is an average blood glucose in a period after the fasting starts read by the real-time CGMS, and the TI is the time between the current high-dose injection and the midpoint of the previous high-dose injection.

2. The cloud big data-based system for insulin pump individualized configuration optimization according to claim 1, wherein the user's personal information and the user's historical data stored in the cloud big data server comprise a name, a gender, an age, and a contact number of the user, a serial number of the insulin pump, records of an insulin pump infusion dose, an insulin pump infusion time and an insulin pump infusion rate, a blood glucose output value BG and a data measurement time (Ts) corresponding to the BG, the carbohydrate intake, a sleep and an exercise recorded by the user.

3. The cloud big data-based system for insulin pump individualized configuration optimization according to claim 1, wherein the cloud big data server optimizes the CR, the IS, and the TA by collecting a real-time data obtained by the user using the real-time CGMS and the insulin pump for the high-dose injection, specific steps are as follows:

step A, establishing a regression equation $$BGbefore - BGafter = (BOLUS + BOLUSprev)IS + (-CARBS)\frac{IS}{CR} + (-BOLUSprev \times \min(TI, TA))\frac{IS}{TA}$$

wherein, BGbefore is the blood glucose value before the high-dose injection and equal to BGcurrent in the calculation formula for the BOLUS; BGafter is a measured blood glucose value after a period of the high-dose injection;

step B, obtaining the following data near each high-dose injection start time (Tstart) from the insulin pump and the real-time CGMS through the smart phone:
the injection start time Tstart: insulin pump data
an injection end time/Tend): insulin pump data
the injection volume BOLUS of the high-dose injection at the Tstart: insulin pump data
the blood glucose value BGbefore measured by the implantable glucose sensor at the Tstart the blood glucose value BGafter measured by the implantable glucose sensor after a period of Tend
the carbohydrate intake CARBS input by the user near the Tstart
forming a sample record packet for a calculation $$[Tstart_n, Tend_n, BOLUS_n, CARBS_n, BGbefore_n, BGafter_n]$$

data in the last three to six months are used for a regression, a subscript number n of a historical data variable is arranged in reverse order of the Tstart;
step C, constructing a sample matrix:

$$G = \begin{bmatrix} \Delta BG_1 \\ \Delta BG_2 \\ \Delta BG_3 \\ \vdots \\ \Delta BG_n \end{bmatrix} \quad X = \begin{bmatrix} BOLUS'_1 & -CARBS_1 & -BOLUS_2 \times TI'_1 \\ BOLUS'_2 & -CARBS_2 & -BOLUS_3 \times TI'_2 \\ BOLUS'_3 & -CARBS_3 & -BOLUS_4 \times TI'_3 \\ \vdots & \vdots & \vdots \\ BOLUS'_n & -CARBS_n & -BOLUS_{n+1} \times TI'_n \end{bmatrix}$$

wherein, $\Delta BG_n = BGafter_n - BGbefore_n$, when $TI_n < TAu$, $BOLUS'_n = BOLUS_n + BOLUS_{n+1}$, $TI'_n = TI_n$, $TI_n = Tstart_n - (Tstart_{n+1} + Tend_{n+1})/2$;

when $TI_n > TAu$, $BOLUS'_n = BOLUS_n$, $TI'_n = 0$;
when $TAl \leq TI_n \leq TAu$, the sample is abandoned;
TAu is an upper limit allowed by the TA, and TAl is a lower limit allowed by the TA;
step D, if for each n, $X_{n,3} = 0$, then:

$$X = \begin{bmatrix} BOLUS'_1 & -CARBS_1 \\ BOLUS'_2 & -CARBS_2 \\ BOLUS'_3 & -CARBS_3 \\ \vdots & \vdots \\ BOLUS'_n & -CARBS_n \end{bmatrix} \quad C = \begin{bmatrix} IS \\ IS/CR \end{bmatrix}$$

otherwise, the sample matrix remains unchanged;
step E, solving an overdetermined equation G=XC, a weighted least square method is used to solve: $\hat{C} = (X^T W X)^{-1} X^T W G$;
step F, eliminating an abnormal data: calculating a residual error: $\hat{\varepsilon} = G - X\hat{C}$, eliminating data items whose residual error is greater than a threshold, and then repeating a regression algorithm in the steps A-F until there are no data items whose residual error is greater than the threshold;
step G, calculating updated physiological parameters IS, CR, and TA according to results of the regression algorithm:

$\widehat{IS} = \hat{C}_{1,1}$ $\widehat{CR} = \hat{C}_{1,1}/\hat{C}_{2,1}$ if $\hat{C}_{3,1}$ exists, then $\widehat{TA} = \hat{C}_{1,1}/\hat{C}_{3,1}$, otherwise $\widehat{TA} = TA$;

step H, finally, using the obtained $\widehat{IS}$, $\widehat{Cr}$ and $\widehat{Ta}$ to correct the currently set IS, CR and TA with a predetermined correction ratio γ, wherein a range of γ values is 0<γ<1, $IS := (1-\gamma) \times IS + \gamma \times \widehat{IS}$ $CR := (1-\gamma) \times CR + \gamma \times \widehat{CR}$ $TA := (1-\gamma) \times TA + \gamma \times \widehat{TA}$ the above is used as setting parameters for the high-dose injection of the insulin pump from now on;
TAl and TAu are revised at the same time:

$TAl := TA \times \tau\%$, where $0 < \tau < 100$;

$TAu := TA \times \upsilon\%$, where $100 < \upsilon < 150$;

storing and updating physiological parameters IS, CR, TA, TAl and TAu to the cloud big data server and pushing the physiological parameters to a mobile application and the insulin pump.

4. The cloud big data-based system for insulin pump individualized configuration optimization according to claim 1, wherein the cloud big data server optimizes a value of physiological parameter GR in predetermined time periods and the corresponding basal infusion rate BASAL by collecting real-time data obtained by the user using the real-time CGMS and the insulin pump in real time, specific steps are as follows:

step A, first, segmenting 24 hours a day according to the basal infusion rate established by the user with reference to doctor's recommendations and his/her own situation, wherein the GR and the BASAL values in each time period need to be set and calculated independently, for each time period and 2 hours before the each time period, if the user eats something, and a high-dose injection accompanied with or without food is performed, data obtained at 2 hours after [a] meal or the high-dose injection needs to be excluded from the time period, data of the time period is updated to only include data of longer continuous time remaining after a removal of the data obtained at 2 hours after the meal/high-dose injection;

step B, collecting sample data in each valid time period:
Tstart: the start time of the time period
BGstart: an average value of blood glucose in a previous short period of the time period
BGend: an average value of blood glucose in a last short period of the time period
BASAL: the basal infusion rate during the time period
t: a duration of the time period
IS: the insulin sensitivity index
TA: the insulin retention time $$RESIDUAL = BOLUSprev\left(1 - \frac{\min(TL,TA)}{TA}\right):$$

residual insulin in the body at the beginning of the time period
SNR: a signal-to-noise ratio of dynamic blood glucose data
forming a sample record package for a calculation $[Tstart_n, BGstart_n, BGend_n, BASAL_n, t_n, RESIDUAL_n, SNR_n]$ and system parameters $IS$ and $TA$;

data of the time period in the last three to six months are used for [a] regression, and the subscript number n of the historical data variables is arranged in reverse order of the Tstart;

step C, for each effective time period, considering an effectiveness of ingesting insulin, a total glucose $\Delta BG$ released by [a] body into the blood through metabolism is:

$\Delta BG_n = BGend_n - BGstart_n + [BASAL_n \times t_n + RESIDUAL_n] \times IS$ establishing a regression equation $\Delta BG = GR \times t$;

step D, for each valid time period, using a regression method to calculate an updated value $\widehat{GR}$ of GR $$\widehat{GR} = \frac{\sum_{n=1}^{N} t_n \times \Delta BG_n \times SNR_n \times w(T'_n)}{\sum_{n=1}^{N} t_n^2 \times SNR_n \times w(T'_n)}$$

wherein, $w(T')$ is a first time-related weight, $T'_n = Tcurrent - Tstart_n$, Tcurrent is the current time, that is, the time of the latest historical data $Tstart_1$;

step E, using the updated value $\widehat{GR}$ to correct the currently set GR with a predetermined correction ratio $\gamma$ $GR := (1-\gamma) \times GR + \gamma \times \widehat{GR}$ a range of $\gamma$ values is $0 < \gamma < 1$;

step F, using a modified GR and a historical sample packet $[BGstart_n, t_n, RESIDUAL_n]$ of the time period to calculate value $\widehat{BASAL}'_n$ to be set in the time period a correction according to the formula:

$$\widehat{BASAL}'_n = \frac{\frac{BGstart_n - BGtarget + GR \times t_n}{IS} - RESIDUAL_n}{t_n}$$

step G, weighting all the calculated $\widehat{BASAL}'_n$ in time to calculate a current BASAL correction value $\widehat{BASAL}$:

$$\widehat{BASAL} = \frac{\sum_{n=1}^{N} \widehat{BASAL}'_n \times w'(T'_n)}{\sum_{n=1}^{N} w'(T'_n)}$$

wherein, w'(T') is a second time-related weight;
step H, if a difference between the calculated value $\widehat{BASAL}$ and the current BASAL value exceeds the threshold, using the [calculated] $\widehat{BASAL}$ to correct the currently set BASAL with a predetermined correction $\gamma$:

$\gamma: BASAL := (1 - \gamma) \times BASAL + \gamma \times \widehat{BASAL}$ a range of $\gamma$ values is $0 < \gamma < 1$;
storing and updating the BASAL as a setting parameter of a basal injection rate of the insulin pump, and storing the BASAL to the cloud big data server together with the physiological parameter GR and push the BASAL and the GR to the mobile application and the insulin pump.

5. The cloud big data-based system for insulin pump individualized configuration optimization according to claim 1, wherein the cloud big data server optimizes the basal infusion rate BASAL in predetermined time periods by collecting real-time data obtained by the user using the real-time CGMS and the insulin pump in real time, specific steps are as follows:

step A, first, segmenting 24 hours a day according to the basal infusion rate established by the user with reference to doctor's recommendations and his/her own situation, wherein the BASAL value in each time period needs to be set and calculated independently, for each time period and 2 hours before the each time period, if the user eats something, and a high-dose injection accompanied with or without food is performed, data obtained at 2 hours after [a] meal or the high-dose injection needs to be excluded from the time period, data in the time period is updated to include only data of the [longer] continuous time remaining after a removal of the data [obtained] at 2 hours after the eating/high-dose injection;

step B, collecting sample data in each valid time period:

the Tstart: the start time of the time period the BGstart: the average value of blood glucose in a previous short period of the time period BGend: an average value of blood glucose in a last short period of the time period BASAL: basal infusion rate during the time period t: a duration of the time period IS: the insulin sensitivity index TA: the insulin retention time $$RESIDUAL = BOLUSprev\left(1 - \frac{\min(TI,TA)}{TA}\right);$$

a residual insulin in [a] body at the beginning of the time period forming a sample record package for a calculation

[$Tstart_n, BGstart_n, BGend_n, BASAL_n, t_n, RESIDUAL_n$] and system parameters $IS$ and $TA$;

the data of the time period in the last three to six months are used for [a] regression, and the subscript number n of historical data variables is arranged in reverse order of the Tstart;

step C, for an $n^{th}$ time period, using a historical sample packet of the $n^{th}$ time period to calculate value $BASAL'_n$ to be set in the time period after a correction according to the formula:

$$BASAL'_n = BASAL_n + \frac{RESIDUAL_n}{t_n} - \frac{BGtarget - BGend_n}{IS \times t_n}$$

step D, weighting all the calculated $BASAL'_n$ in time to calculate a current BASAL correction value $BASAL'$:

$$BASAL' = \frac{\sum_{n=1}^{N} BASAL'_n \times w'(T'_n)}{\sum_{n=1}^{N} w'(T'_n)}$$

wherein, w'(T') is a time-related weight

Step E, if a difference between difference between the calculated value $BASAL'$ and the current BASAL value exceeds a threshold, using the [calculated] $BASAL'$ to correct the currently set BASAL with a predetermined correction ratio γ:

$$\gamma: BASAL := (1 - \gamma) \times BASAL + \gamma \times BASAL'$$

a range of γ values is 0<γ<1.

6. A cloud big data-based method for insulin pump individualized configuration optimization, comprising:

step 1, obtaining, by a smart phone application, a cloud big data server data when a system is started to determine whether a user is using an insulin injection system for the first time, if yes, prompting the user to set parameters insulin sensitivity index (IS), an amount of carbohydrate converted by 1 unit of insulin (CR), insulin retention time (TA), a glucose release rate (GR) during fasting via metabolism, time segmentation and a basal injection rate or to continue to use a default setting, if no, downloading updated parameters from a cloud big data server;

step 2, entering into a high-dose injection mode in response to the user inputting a high-dose injection command manually, step 3, in the high-dose mode, the insulin pump prompting the user to manually enter a carbohydrate intake (CARBS) and confirm a target blood glucose value to be achieved through the smart phone application, while obtaining a current blood glucose value (BGcurrent) measured by a real-time continuous glucose monitoring system (CGMS);

step 4, calculating a required high-dose injection volume (BOLUS) using previously set or obtained parameter values:

BOLUS=CARBS/$CR$+($BG$current−$BG$target)/$IS$−BOLUSprev[1−min($TI,TA$)/$TA$], wherein BGtarget is a target blood glucose value, and BOLUSprev is an injection volume of a previous high-dose injection, TI is a time between a current high-dose injection and a midpoint of the previous high-dose injection, min (TI, TA) is a smaller value of the TI and the TA, so that when the TI is greater than or equal to the TA, a residual amount of the previous high-dose injection $$BOLUSprev\left(1 - \frac{\min(TI,TA)}{TA}\right)$$

is 0, and calculating a basal infusion rate (BASAL), wherein the BASAL is counted in insulin units per hour (U/h), during a fasting period (t) as follows:

$$BASAL = \frac{\frac{BGstart - BGtarget + GR \times t}{IS} - BOLUSprev\left(1 - \frac{\min(TI,TA)}{TA}\right)}{t}$$

wherein, BGstart is an average blood glucose in a period after the fasting starts read by the real-time CGMS;

step 5, prompting the user to confirm an infusion volume and a high-dose infusion time, and calculating an injection stop time Tend=Tstart+TBolus, wherein TBolus=infusion volume/bolus-rate, bolus-rate is a user-defined high-dose insulin infusion rate, and Tstart is an injection start time;

step 6, uploading insulin injection information Tstart, Tend, BOLUS, CARBS and CGMS blood glucose monitoring data to the cloud big data server;

step 7, downloading the insulin injection information at the insulin pump and performing the high-dose injection until the Tend is reached;

step 8, detecting whether there are physiological parameters updated in the cloud big data server, if yes, updating local storage parameters, and then repeating step 2; if no, repeating step 2 directly.

* * * * *